United States Patent
Kano et al.

[11] Patent Number: 5,294,304
[45] Date of Patent: Mar. 15, 1994

[54] PROCESS FOR THE RECOVERY OF ABSOLUTE ETHANOL BY VAPOR COMPRESSION EXTRACTIVE DISTILLATION

[75] Inventors: Yoshikazu Kano, Yokohama; Hirotoshi Horizoe, Hiroshima; Tetsuya Tanimoto, Hiroshima; Itsuo Yamamoto, Hiroshima, all of Japan

[73] Assignee: Ministry of International Trade and Industry, Tokyo, Japan

[21] Appl. No.: 29,961

[22] Filed: Mar. 9, 1993

Related U.S. Application Data

[63] Continuation of Ser. No. 721,568, Jul. 29, 1991, abandoned.

[30] Foreign Application Priority Data

Nov. 14, 1989 [JP] Japan .................................. 1-294032

[51] Int. Cl.$^5$ ........................................ B01D 3/40
[52] U.S. Cl. ................................ 203/19; 203/26; 203/49; 203/70; 203/78; 203/80; 203/DIG. 13; 568/916; 568/918
[58] Field of Search .............. 203/19, 26, 24, DIG. 13, 203/71, 73, 84, 78, 70, 49, 80; 568/916, 918

[56] References Cited

U.S. PATENT DOCUMENTS

| | | | |
|---|---|---|---|
| 2,619,814 | 12/1952 | Kniel | 203/26 |
| 3,187,066 | 1/1965 | Nathan | 203/26 |
| 4,303,478 | 12/1981 | Field | 203/26 |
| 4,340,446 | 7/1982 | Crawford | 203/19 |
| 4,428,798 | 10/1984 | Zudkevitch et al. | 203/19 |
| 4,600,477 | 7/1986 | Higashi et al. | 203/19 |
| 4,636,284 | 1/1987 | English et al. | 203/19 |
| 4,718,986 | 1/1988 | Comiotto et al. | 203/26 |
| 4,956,052 | 9/1990 | Hirati et al. | 203/19 |
| 5,035,776 | 7/1991 | Knapp et al. | 203/26 |

FOREIGN PATENT DOCUMENTS

| | | | |
|---|---|---|---|
| 2-184643 | 7/1990 | Japan | 203/19 |
| 3-005431 | 1/1991 | Japan | 203/19 |
| 3-005432 | 1/1991 | Japan | 203/19 |

Primary Examiner—Wilbur Bascomb, Jr.
Attorney, Agent, or Firm—Wenderoth, Lind & Ponack

[57] ABSTRACT

This invention relates to a process for the production of absolute alcohol from aqueous alcohol, whereby saving of energy to a greater extent is rendered possible in a more simple process, as compared with the prior art azeotropic distillation method using benzene or cyclohexane. That is, aqueous alcohol is subjected to extractive distillation in a first distillation column under such a condition that a liquid and gas of a solvent simultaneously coexist using low pressure propane, propylene and butane as the solvent, absolute alcohol substantially free from water is recovered from the bottom of the distillation column and subjected to stripping of hydrocarbons in a second distillation column, during which the gaseous phases of the first and second distillation columns are mixed and compressed, utilized through recompression as a heat source of a reboiler of the first distillation column, subjected to separation of water content and recycled to the upper parts of the first and second distillation columns. In accordance with the process, the energy required can largely be reduced.

In Examples, the energy required for producing 1 kg of absolute alcohol is reduced to 1/5 to 1/10 of the prior art azeotropic distillation method, which shows the advantages of the present invention.

According to the process of the present invention, installations such as compressors, heat exchangers, decanters, etc. can be omitted and the installation cost can be reduced by about 30%.

1 Claim, 2 Drawing Sheets

PROCESS FOR THE RECOVERY OF ABSOLUTE ETHANOL BY VAPOR COMPRESSION EXTRACTIVE DISTILLATION

This application is a continuation of now abandoned application, Ser. No. 07/721,568, filed Jul. 29, 1991.

TECHNICAL FIELD OF INVENTION

This invention relates to a process for concentrating and purifying alcohol and more particularly, it is concerned with a process suitable for obtaining high purity alcohol with energy saving by concentrating and purifying synthetic alcohols, waste aqueous alcohol solutions in the food industry, fermented alcohols, etc.

TECHNICAL BACKGROUND

Fermented alcohols from carbohydrates such as sweet potatoes, corns, etc. are important raw materials for drinking or industrial use, but an aqueous alcohol solution obtained by the fermentation method has a low alcohol concentration, i.e. 10 to 20% by weight and accordingly, it is required to concentrate it to about 95 to 100% by weight.

Up to the present time, a distillation method has been employed as the concentrating method, but this distillation method is not economical because of difficulty in recovering the evaporation latent heat of alcohol and water, as a predominant component. Thus, it has eagerly been desired to develop a concentrating method of the energy saving type.

In the conventional distillation method, an energy level corresponding to about 3000 kcal/kg·alcohol is required for concentrating alcohol from 10% by weight to 95% by weight. For concentrating alcohol from 95% by weight to absolute alcohol of at least 99.2% by weight, azeotropic distillation using diethyl ether, benzene or cyclohexane has been carried out with about 1000 to 2000 kcal/kg·alcohol. Thus, energy saving is also desired.

On the other hand, there has been proposed a method comprising extracting and separating alcohol from water by the use of carbon dioxide under supercritical state or pseudocritical state, thereby concentrating the alcohol, as a concentrating method of the energy saving type (Japanese Patent Laid-Open Publication Nos. 56201/1981 and 141528/1984).

In the case of using carbon dioxide as a solvent, however, it has lately been reported that the solubility of alcohol is so low that a large amount of carbon dioxide is required, the selective extraction of alcohol is limited and the maximum alcohol concentration is limited to about 91% by weight. According it is impossible to obtain a concentration exceeding this limit.

DISCLOSURE OF THE INVENTION

The present invention aims at providing a process for concentrating alcohol to a degree of concentration of 99% by weight or more with much less energy as compared with the distillation method of the prior art.

That is, the inventors have made various studies on a process for producing absolute alcohol with a purity of at least 99% by weight, being valuable on the alcohol market with energy saving and consequently, have found that absolute alcohol can readily be obtained by adding a hydrocarbon solvent consisting of propane, propylene, n-butane, i-butane or mixtures thereof, as an extracting solvent, to an aqueous alcohol solution as a raw material, and then subjecting the mixture to pressurized extractive distillation and/or supplying the most part of the heat source of the pressurized extractive distillation column by the compressive heat generated during recompressing and recycling the overhead gas of the pressurized extractive distillation column, whereby energy can be saved as compared with the prior art distillation method. The present invention is based on this finding.

That is, the present invention provides a process for the production of absolute alcohol, which comprises feeding a raw material containing ethanol and water, as predominant components, to the middle part of a first distillation column, feeding a hydrocarbon solvent, preferably hydrocarbons of $C_3$–$C_4$, to the upper part of the first distilling column, maintaining the hydrocarbons at such a temperature and pressure that the liquid and gas of the hydrocarbon are simultaneously present in the first distilling column, withdrawing ethanol and liquid hydrocarbons, substantially free from water content, from the lower part of the first distillation column and withdrawing water and vapor hydrocarbons, substantially free from ethanol, from the upper part of the distillation column, characterized in that when the mixed solution of absolute alcohol and hydrocarbons at the lower part of the first distillation column is fed to a second distillation column, where the hydrocarbon solvent is stripped, the gaseous phase at the upper part of the second distillation column is mixed with the gaseous phase at the upper part of the first distillation column and compressed, after using the compression heat thereof as a heat source of the first distillation column, the mixture is cooled and liquefied, and after the water content is separated, it is recycled to the upper parts of the second distillation column and the first distillation column.

BEST EMBODIMENT FOR CARRYING OUT THE PRESENT INVENTION

Figure 1:
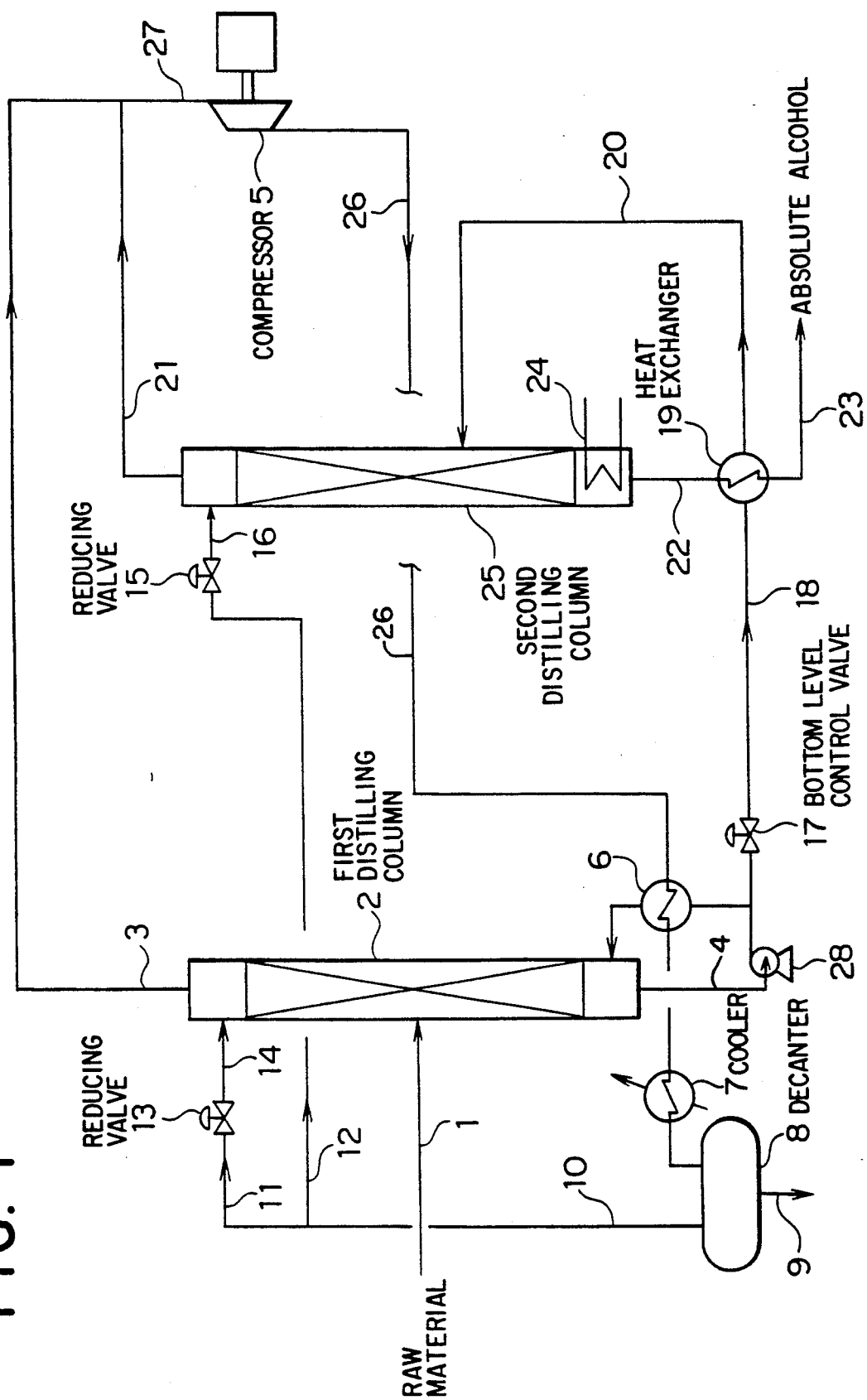
FIG. 1 is a process flow diagram for carrying out the present invention.

One embodiment of the present invention will now be illustrated in detail by FIG. 1 to clarify the actions thereof.

Referring to FIG. 1, an aqueous alcohol solution, as a raw material, from a feed line 1 is fed to the middle part of a first distillation column 2 and a hydrocarbon solvent is fed to the upper part of the first distillation column 2 from a line 14. When the aqueous alcohol solution is allowed to be present under such a condition that the gas and liquid of the hydrocarbons coexist, the alcohol is selectively extracted by the liquid hydrocarbons. Under such a condition that the liquid hydrocarbon is present in a relatively larger amount than the alcohol, water content is hardly dissolved in a mixed liquid solution of the hydrocarbon and alcohol and the water content can be selectively transferred to the hydrocarbon gas phase side by providing such a condition that the water concentration in the hydrocarbon gas phase is less than the saturated concentration of water. As the hydrocarbon, it is preferable to use propane, propylene, n-butane or i-butane in view of the interaction of alcohol or water with the hydrocarbon. Thus, the alcohol and water can be separated to obtain absolute alcohol.

For the purpose of obtaining the provision that both the gas and liquid of the hydrocarbon coexist in the first distillation column 2 for effecting the pressurized extraction, it is required to adjust the temperature to at most about the critical temperature Tc of the hydrocarbon and the pressure to the saturated vapor pressure of the hydrocarbon at this temperature (maximum value: about critical pressure Pc). The ratio of the gas and liquid of the hydrocarbon should be varied depending upon the concentrations of the alcohol in the raw material and the absolute alcohol in the product and can be controlled by the recycling quantity of the hydrocarbon and the mode of giving heat quantity to a reboiler 6.

The above described conditions in the first distillation column are varied with the solvent to be used, but in general, the following conditions are preferably employed.

| Solvent | Critical Temperature (°C.) | Critical Pressure (atm) | Commonly Used Range under Gas-liquid Coexisting Conditions* | | Ordinary Range of Gas/Liquid Weight Ratio** |
|---|---|---|---|---|---|
| | | | Temp. (°C.) | Pressure (atm) | |
| $C_3H_6$ | 92.3 | 45.0 | 20~92 | 10~45 | 6~20 |
| $C_3H_8$ | 96.8 | 42.0 | 20~96 | 8~42 | 6~20 |
| n-$C_4H_{10}$ | 152.0 | 37.5 | 20~152 | 2~37 | 6~20 |
| i-$C_4H_{10}$ | 135.0 | 36.0 | 10~135 | 3~36 | 6~20 |

Note)
*strictly, saturated vapor pressure at the temperature and composition
**For example, when water-containing alcohol ($C_2H_5OH$ 100 kg/h, $H_2O$ 5 kg/h) and propane (2100 kg/h) are fed to the first distillation column, an overhead gas ($C_3H_8$ 2000 kg/h, $H_2O$ 4.9 kg/h) is withdrawn from the overhead part and a bottom liquid ($C_3H_8$ 100 kg/h, $C_2H_5OH$ 100 kg/h, $H_2O$ 0.1 kg/h) is withdrawn from the bottom part, during which gas/liquid weight ratio = 2004.9/200.1 = 10.0.

The overhead gas (consisting of a hydrocarbon gas and water, substantially free from alcohol) of the first distillation column for effecting the pressurized extraction is taken out of a line 3, recompressed by a compressor 5 and guided to a reboiler 6 through a line 26, during which the compression heat generated by the recompression of the overhead gas is preferably used as a heat source of the reboiler 6. This operation can be carried out while maintaining the temperature difference between the overhead and bottom of the first distillation column within at most 10° C., so that the temperature of the overhead gas can be raised to that of the bottom or higher by a slight compression of the overhead gas at the compressor 5, i.e. a slight power and the latent heat of condensation of the overhead gas can sufficiently be utilized as a heat source of the reboiler 6. Accordingly, saving of energy can be done in this way to a larger extent as compared with the prior art distillation method.

When the overhead temperature of the first distillation column 2 is T °C., the bottom temperature is generally about (T+4)~(T+6), so the temperature of the overhead gas (T °C.) is raised to give such at least a temperature difference (about 5° C.) as to be heat-exchanged with the bottom liquid (about T+5° C.) utilizing the temperature raising effect by adiabatic compression at the compressor 5. That is, the compression is carried out by the compressor 5 in such a manner that the gas temperature is raised from T °C. to about (T+10) °C. To this end, the compression ratio (outlet pressure/inlet pressure) is ordinarily adjusted to 1.2 to 1.5. The compressed gas is condensed at (T+10) °C. and all of the latent heat of condensation and a part of the sensible heat thereof are given to the bottom liquid of the first distillation column, whereby the substantial energy required for the distillation can almost be given.

The mixture of the hydrocarbon and water, heat-exchanged at the reboiler 6, is fed through a cooler 7 to a decanter 8, where the water content and hydrocarbon are subjected to separation by gravity-settling. The water is withdrawn through a line 9, and the hydrocarbon substantially free from water is recycled to the first distillation column 2 for pressurized extraction and the second distillation column 25 for stripping through lines 10, 11 and 12, reducing valves 13 and 15, and lines 14 and 16.

The mixture of absolute alcohol substantially free from water and liquid hydrocarbon is withdrawn from a bottom liquid withdrawing line 4 of the first distillation column 2, guided to a heat-exchanger 19 through a line 18 provided with a bottom level controlling valve 17 of the first column 2, heated and further fed through a line 20 to the middle part of the second distillation column 25 functioning as a stripper. This second distillation column is also a pressurized column in which the gas-liquid contact part consists of a packed column, perforated plate or tray. The pressure of the second distillation column 25 is preferably so maintained that the pressure difference from the first distillation column 2 is substantially zero or as small as possible.

The overhead gas (hydrocarbon gas substantially free from alcohol) of the second distillation column 25 is taken out of a line 21, mixed with the gas of the line 3 of the first distillation column 2 and recompressed by the compressor 5.

The inventors have confirmed that it is more economical to recompress the gases of the lines 3 and 21 by one compressor than by separate recompressing and thus the feature of the present invention consists in effecting the operation as in the former case.

As described above, it is confirmed in practicing the present invention that the smaller the pressure difference between the first distillation column 2 and the second distillation column 25, the smaller is the energy required for compressing and the operation is most economical when the difference is zero. In a preferred embodiment of the present invention, provision of such conditions is carried out.

On the other hand, absolute alcohol substantially containing no hydrocarbon (at least 99.2 weight % of ethanol) is withdrawn from the bottom of the the second distillation column 25 via a line 22. Since the temperature of the absolute alcohol withdrawn from the line 22 is substantially the same as the boiling point of alcohol under pressure, the absolute alcohol is guided to the heat exchanger 19 via the line 22, where the heat thereof is recovered and utilized for raising the temperature of the fluid of the line 18, and it is withdrawn as a product. 24 Designates a reboiler of the second distillation column 25.

The present invention will now be illustrated in detail by the following examples.

height: 4 m
packed column

Thus, it is confirmed that the energy required and installation cost can largely be decreased according to the present invention.

TABLE 1

Figure 2:
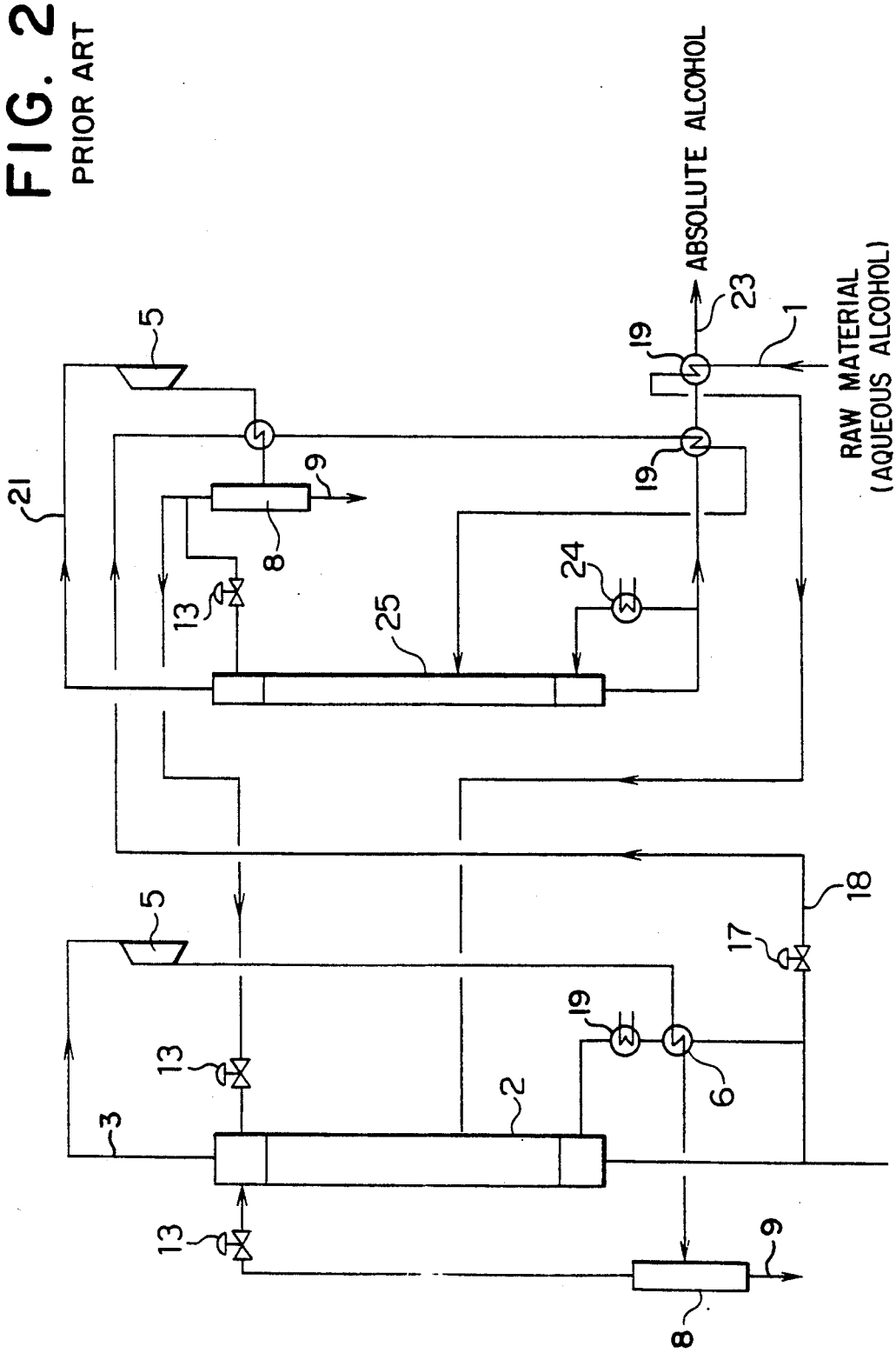
FIG. 2 is a process flow diagram before the improvement according to the present invention.

| Hydrocarbon Solvent | Propane | | Propane | | Propylene | | n-Butane | | i-Butane | |
|---|---|---|---|---|---|---|---|---|---|---|
| RUN No. | 1-1 | 1-2 | 1-3 | 1-4 | 2-1 | 2-2 | 3-1 | 3-2 | 4-1 | 4-2 |
| 1) Process Flow | FIG. 2 | FIG. 1 | FIG. 2 | FIG. 1 | FIG. 2 | FIG. 1 | FIG. 2 | FIG. 1 | FIG. 2 | FIG. 1 |
| 2) Raw Material | | | | | | | | | | |
| Flow Rate (kg/h) | 0.1 | 0.1 | 0.1 | 0.1 | 0.1 | 0.1 | 0.1 | 0.1 | 0.1 | 0.1 |
| Alcohol Concentration (wt %) | 95 | 95 | 95 | 95 | 95 | 95 | 95 | 95 | 95 | 95 |
| 3) First Distillation Column | | | | | | | | | | |
| Pressure (kg/cm$^2$G) | 9 | 9 | 33 | 33 | 9 | 9 | 1 | 1 | 1.5 | 15 |
| Temperature (°C.) Overhead | 26 | 26 | 83 | 83 | 20 | 20 | 20 | 20 | 17 | 17 |
| Temperature (°C.) Bottom | 30 | 30 | 88 | 88 | 25 | 25 | 24 | 24 | 21 | 21 |
| Solvent Flow Rate (kg/h) | 5 | 5 | 2 | 2 | 5 | 5 | 5 | 5 | 5 | 5 |
| 4) Second Distillation Column | | | | | | | | | | |
| Pressure (kg/cm$^2$G) | 8 | 9 | 8 | 33 | 8 | 8 | 1 | 1 | 1.5 | 1.5 |
| Temperature (°C.) Overhead | 25 | 26 | 25 | 83 | 16 | 16 | 20 | 20 | 17 | 17 |
| Temperature (°C.) Bottom | 150 | 150 | 150 | 207 | 150 | 150 | 97 | 97 | 105 | 105 |
| Reflux Ratio | 0.5 | 0.5 | 0.5 | 0.5 | 0.5 | 0.5 | 0.5 | 0.5 | 0.5 | 0.5 |
| Energy Required (kcal/kg alcohol) | 210 | 200 | 195 | 180 | 209 | 183 | 215 | 185 | 214 | 181 |
| Comparison of Installation Cost (—) | 100 | 68 | 100 | 70 | 100 | 72 | 100 | 69 | 100 | 70 |
| Concentration of Product Ethanol (wt %) | 99 or more | ← | ← | ← | ← | ← | ← | ← | ← | ← |
| Recovery of Product Ethanol (wt %) | 99 or more | ← | ← | ← | ← | ← | ← | ← | ← | ← |

Note:
In Tables 1 and 2, the left arrow symbol (←) signifies that the data are the same as the data to the left in the same row.

EXAMPLE 1

The process of the present invention shown in the flow diagram of FIG. 1 is compared with the reference process, before improved as in the present invention, shown in the flow diagram of FIG. 2 (A process comprising compressing separately the gaseous phases leaving the upper parts of the first distillation column 2 and second distillation column 25 by means of different compressor 5,5 and utilizing respectively the heat thereof as heat sources of the distillation columns; the same numerals in FIG. 2 as in FIG. 1 representing the same apparatus. Thus, the system of FIG. 2 is clearly different from that of the present invention with respect to using the two compressors.) using propane, propylene, n-butane and i-butane as the hydrocarbon solvent, as to the energy required, installation cost and product alcohol concentration, thus obtaining results as shown in Table 1.

The specification of the main instruments is as follows:
First Distillation Column:
 inner diameter: 100 mm
 height: 4 m
 packed column system
Second Distillation Column:
 inner diameter: 100 mm

COMPARATIVE EXAMPLE 1

Procedure of Example 1 was repeated except using $CO_2$, $C_2H_6$, n—$C_6H_{14}$ and benzene as a solvent in the flow of FIG. 1 to obtain results as shown in Table 2.

When using these solvents, the ethanol concentration in the product was not increased and there was not obtained absolute alcohol with a concentration of at least 99.2% by weight.

TABLE 2

| Solvent | $CO_2$ | | $C_2H_6$ | | n-$C_6H_{14}$ | | | Benzene | | |
|---|---|---|---|---|---|---|---|---|---|---|
| RUN No. | 5-1 | 5-2 | 6-1 | 6-2 | 7-1 | 7-2 | 7-3 | 8-1 | 8-2 | 8-3 |
| 1) Process Flow | FIG. 1 | ← | ← | ← | ← | ← | ← | ← | ← | ← |
| 2) Raw Material | | | | | | | | | | |
| Flow Rate (kg/h) | 0.1 | ← | ← | ← | ← | ← | ← | ← | ← | ← |
| Alcohol Concentration (wt %) | 95 | ← | ← | ← | ← | ← | ← | ← | ← | ← |
| 3) First Distillation Column | | | | | | | | | | |
| Pressure (kg/cm$^2$G) | 50 | 50 | 36 | 36 | 1 | 1 | 5 | 1 | 1 | 5 |
| Temperature (°C.) Overhead | 20 | 20 | 20 | 20 | 94 | 94 | 140 | 106 | 106 | 152 |
| Temperature (°C.) Bottom | 31 | 32 | 33 | 35 | 104 | 105 | 160 | 122 | 124 | 165 |
| Solvent Flow Rate (kg/h) | 5 | ← | ← | ← | ← | ← | ← | ← | ← | ← |
| Concentration of Product Ethanol (wt %) | 90 | 91 | 92 | 89 | 95 | 95 | 94 | 94 | 94 | 93 |

UTILITY AND POSSIBILITY ON COMMERCIAL SCALE

In the production of absolute alcohol by separating water content from an aqueous alcohol solution, according to the present invention as described above in detail, absolute alcohol with a purity of at least 99.2% by weight, capable of satisfying the Government Monopoly in Alcohol Act and JIS Standard, can readily be obtained by carrying out pressurized extractive distillation using propane, propylene or butane as a hydrocarbon solvent, and saving of energy can be accomplished to a greater extent by a heat pump system utilizing the recompression heat of the overhead gas, as compared with the prior art distillation method.

We claim:

1. A process for the production of absolute ethanol, which comprises
    feeding a raw material containing ethanol and water, as predominant components, to the middle part of a first distillation column,
    feeding a hydrocarbon solvent to the upper part of the first distillation column, maintaining the hydrocarbon solvent at such a temperature and pressure that a liquid phase and a gas phase of the hydrocarbon solvent are simultaneously present in the first distillation column,
    withdrawing a liquid mixture comprising ethanol and hydrocarbon solvent, substantially free from water content, from the bottom of the first distillation column,
    withdrawing a first gas comprising water and hydrocarbon solvent, substantially free from ethanol, from the top of the first distillation column,
    feeding the liquid mixture of ethanol and hydrocarbon solvent from the bottom of the first distillation column into a second distillation column,
    stripping the hydrocarbon solvent from the ethanol in the second distillation column and withdrawing absolute ethanol from the bottom of the second distillation column;
    withdrawing a second gas comprising hydrocarbon solvent from the top of the second distillation column and forming a gaseous mixture with the first gas from the top of the first distillation column,
    compressing the gaseous mixture of the first and second gases and using at least some of the recompression heat thereby produced as a heat source for the first distillation column,
    cooling and liquifying the gaseous mixture of the first and second gases,
    separating the hydrocarbon solvent from the water in the liquified gaseous mixture, and
    recycling the hydrocarbon solvent into the upper parts of the first and second distillation columns.

* * * * *